US006769292B2

(12) United States Patent
Mansky et al.

(10) Patent No.: US 6,769,292 B2
(45) Date of Patent: Aug. 3, 2004

(54) HIGH THROUGHPUT RHEOLOGICAL TESTING OF MATERIALS (75) Inventors: Paul Mansky, San Francisco, CA (US); Damian A. Hajduk, San Jose, CA (US)

(73) Assignee: Symyx Technologies, INC, Santa Clara, CA (US)

(*) Notice: Subject to any disclaimer, the term of this patent is extended or adjusted under 35 U.S.C. 154(b) by 0 days.

(21) Appl. No.: 09/939,149

(22) Filed: Aug. 24, 2001

(65) Prior Publication Data

US 2003/0037601 A1 Feb. 27, 2003

(51) Int. Cl.[7] .............................................. G01N 11/04
(52) U.S. Cl. ................... 73/54.05; 73/54.07; 73/54.02; 73/54.32; 73/54.34
(58) Field of Search ......................... 73/54.05, 54.07, 73/54.02, 54.04, 54.32, 54.34

(56) References Cited

U.S. PATENT DOCUMENTS

| | | | |
|---|---|---|---|
| 1,870,412 A | 8/1932 | Kennedy | 73/54.01 |
| 3,071,961 A | 1/1963 | Heigl et al. | 73/54.08 |
| 3,675,475 A | 7/1972 | Weinstein | 73/89 |
| 3,713,328 A | 1/1973 | Aritomi | 73/54.08 |
| 3,798,960 A | 3/1974 | Glass | 73/54.05 |
| 3,805,598 A | 4/1974 | Corcoran | 73/81 |
| 3,818,751 A | 6/1974 | Karper et al. | 73/788 |
| 3,849,874 A | 11/1974 | Jeffers | 29/590 |
| 3,895,513 A | 7/1975 | Richardson | 73/54.07 |
| 3,908,441 A | 9/1975 | Virloget | 73/54.08 |
| 3,933,032 A | 1/1976 | Tschoegl | 73/781 |
| 4,229,979 A | 10/1980 | Greenwood | 73/704 |
| 4,402,215 A * | 9/1983 | Guastavino | 73/54.01 |
| 4,447,125 A | 5/1984 | Lazay et al. | 350/96.3 |
| 4,517,830 A | 5/1985 | Gunn et al. | 73/54.15 |
| 4,567,774 A | 2/1986 | Manahan et al. | 73/826 |
| 4,570,478 A | 2/1986 | Soong | 73/54.23 |
| 4,599,219 A | 7/1986 | Cooper et al. | 422/61 |
| 4,602,501 A | 7/1986 | Hirata | 73/54.01 |
| 4,605,589 A | 8/1986 | Orphanides | 428/290 |
| 4,680,958 A | 7/1987 | Ruelle et al. | 73/54.07 |
| 4,685,328 A | 8/1987 | Huebner et al. | 73/54.15 |

(List continued on next page.)

FOREIGN PATENT DOCUMENTS

| | | |
|---|---|---|
| EP | 0 317 356 A2 | 5/1989 |
| JP | 402297040 A | 12/1990 |
| WO | WO 96/11878 | 4/1996 |
| WO | WO 98/15501 | 4/1998 |
| WO | WO 99/18431 | 4/1999 |
| WO | WO 00/17413 | 3/2000 |
| WO | WO 00/23921 | 4/2000 |
| WO | WO 0036410 | 6/2000 |
| WO | WO 00/40331 | 7/2000 |
| WO | WO 00/51720 | 9/2000 |
| WO | WO 00/67086 | 11/2000 |
| WO | WO 01/79949 A2 | 10/2001 |

OTHER PUBLICATIONS

"DMA 2980 Dynamic Mechanical Analyer," http://www.tainst.com/dma2.html, Dec. 29, 2000.
"Introducing the New DMTA V!", http://www.rheometric-scientific.com/dmtaV.htm, Dec. 29, 2000.

(List continued on next page.)

Primary Examiner—Hezron Williams
Assistant Examiner—Rodney Frank
(74) Attorney, Agent, or Firm—Dobrusin & Thennisch PC (57) ABSTRACT A library of materials is screened for viscosity. A library of materials is provided. The library is contacted with at least one capillary for applying a force through the materials. The relative flow resistance of the materials is measured in response to the force; and the materials in the library are ranked based on the monitored flow resistance.

18 Claims, 3 Drawing Sheets

U.S. PATENT DOCUMENTS

| | | |
|---|---|---|
| 4,699,000 A | 10/1987 | Lashmore et al. ............. 73/81 |
| 4,715,007 A | 12/1987 | Fujita et al. ................ 364/563 |
| 4,740,078 A | 4/1988 | Daendliker et al. ........ 356/35.5 |
| 4,749,854 A | 6/1988 | Martens ...................... 250/225 |
| 4,789,236 A | 12/1988 | Hodor et al. ................. 356/33 |
| 4,793,174 A | 12/1988 | Yau .......................... 73/54.06 |
| 4,829,837 A | 5/1989 | Telfer ..................... 73/863.01 |
| 4,893,500 A | 1/1990 | Fink-Jensen .............. 73/54.13 |
| 4,899,575 A | 2/1990 | Chu et al. .................. 73/54.08 |
| 4,899,581 A | 2/1990 | Allen et al. .............. 73/150 A |
| 4,926,682 A * | 5/1990 | Holm-Kennedy et al. . 73/54.01 |
| 4,932,270 A | 6/1990 | Lurie et al. ............. 73/862.33 |
| 4,975,320 A | 12/1990 | Goldstein et al. ........... 428/288 |
| 5,008,081 A | 4/1991 | Blau et al. .................... 422/64 |
| 5,051,239 A | 9/1991 | von der Goltz .............. 422/73 |
| 5,092,179 A | 3/1992 | Ferguson .................... 73/790 |
| 5,115,669 A | 5/1992 | Fuller et al. .............. 73/54.39 |
| 5,142,900 A | 9/1992 | Duke ........................ 73/54.39 |
| 5,193,383 A | 3/1993 | Burnham et al. ............ 73/105 |
| 5,236,998 A | 8/1993 | Lundeen et al. .............. 525/52 |
| 5,269,190 A | 12/1993 | Kramer et al. ............... 73/822 |
| 5,271,266 A | 12/1993 | Eschbach ................... 73/54.33 |
| 5,272,912 A | 12/1993 | Katsuzaki ................. 73/54.08 |
| 5,279,149 A * | 1/1994 | Williams et al. .......... 73/54.01 |
| 5,280,717 A | 1/1994 | Hoseney et al. ........... 73/54.22 |
| 5,303,030 A | 4/1994 | Abraham et al. .......... 356/345 |
| 5,305,633 A | 4/1994 | Weissenbacher et al. ...... 73/82 |
| 5,365,776 A * | 11/1994 | Lehmann et al. .......... 73/54.07 |
| 5,398,885 A | 3/1995 | Andersson et al. ......... 244/1 R |
| 5,437,192 A | 8/1995 | Kawamoto et al. ........... 73/826 |
| 5,438,863 A | 8/1995 | Johnson .................... 73/54.02 |
| 5,452,614 A | 9/1995 | Kato et al. ..................... 73/789 |
| 5,452,619 A | 9/1995 | Kawanabe et al. ....... 73/864.01 |
| 5,481,153 A | 1/1996 | Turner ........................ 310/334 |
| 5,517,860 A | 5/1996 | Lin et al. ....................... 79/789 |
| 5,520,042 A | 5/1996 | Garritano et al. .......... 73/54.02 |
| 5,532,942 A | 7/1996 | Kitamura et al. ........... 364/555 |
| 5,610,325 A | 3/1997 | Rajagopal et al. ......... 73/54.39 |
| 5,626,779 A | 5/1997 | Okada ........................ 219/201 |
| 5,699,159 A | 12/1997 | Mason ........................ 356/351 |
| 5,700,953 A | 12/1997 | Hlady et al. ................... 73/105 |
| 5,723,792 A | 3/1998 | Miyazaki ...................... 73/769 |
| 5,728,532 A | 3/1998 | Ackley .......................... 435/6 |
| 5,756,883 A | 5/1998 | Forbes ....................... 73/54.05 |
| 5,764,068 A | 6/1998 | Katz et al. ................... 324/727 |
| 5,776,359 A | 7/1998 | Schultz et al. ........... 252/62.51 |
| 5,817,947 A | 10/1998 | Bergerus ...................... 73/826 |
| 5,821,407 A | 10/1998 | Sekiguchi et al. ......... 73/54.28 |
| 5,847,268 A * | 12/1998 | Ball ........................... 73/54.09 |
| 5,847,283 A | 12/1998 | Finot et al. ................... 73/812 |
| 5,877,428 A | 3/1999 | Scolton ....................... 73/822 |
| 5,892,157 A | 4/1999 | Syre ............................. 73/812 |
| 5,922,967 A | 7/1999 | Motoyama ................... 73/794 |
| 5,959,297 A | 9/1999 | Weinberg et al. ........... 250/288 |
| 5,985,356 A | 11/1999 | Schultz et al. ................. 427/8 |
| 5,999,887 A | 12/1999 | Giannakopoulos et al. ... 702/33 |
| 6,004,617 A | 12/1999 | Schultz et al. ................. 427/8 |
| 6,010,616 A | 1/2000 | Lewis et al. ................. 205/787 |
| 6,013,199 A | 1/2000 | McFarland et al. ... 252/301.4 R |
| 6,030,917 A | 2/2000 | Weinberg et al. ........... 502/104 |
| 6,033,913 A | 3/2000 | Morozov et al. ............. 436/86 |
| 6,034,240 A | 3/2000 | La Pointe ..................... 546/24 |
| 6,034,775 A | 3/2000 | McFarland et al. ......... 356/364 |
| 6,040,193 A | 3/2000 | Winkler et al. ............. 436/180 |
| 6,043,317 A | 3/2000 | Mumick et al. ............. 525/176 |
| 6,043,363 A | 3/2000 | LaPointe et al. ............ 544/225 |
| 6,045,671 A | 4/2000 | Wu et al. .............. 204/298.11 |
| 6,050,138 A | 4/2000 | Lynch et al. .............. 73/150 A |
| 6,050,139 A | 4/2000 | Bousfield et al. ............. 73/150 |
| 6,087,181 A | 7/2000 | Cong .......................... 436/37 |
| 6,092,414 A | 7/2000 | Newman ...................... 73/146 |
| 6,124,476 A | 9/2000 | Guram et al. ............... 549/200 |
| 6,149,882 A | 11/2000 | Guan et al. ................. 422/211 |
| 6,151,123 A | 11/2000 | Nielsen ....................... 356/445 |
| 6,157,449 A | 12/2000 | Hajduk ....................... 356/367 |
| 6,175,409 B1 | 1/2001 | Nielsen et al. .............. 356/337 |
| 6,177,528 B1 | 1/2001 | LaPointe et al. ............ 526/139 |
| 6,182,499 B1 | 2/2001 | McFarland et al. ........ 73/24.06 |
| 6,187,164 B1 | 2/2001 | Warren et al. ................ 205/81 |
| 6,203,726 B1 | 3/2001 | Danielson et al. .... 252/301.4 R |
| 6,225,487 B1 | 5/2001 | Guram ........................ 556/18 |
| 6,225,550 B1 | 5/2001 | Hornbostel et al. ...... 136/236.1 |
| 6,242,623 B1 | 6/2001 | Boussie et al. ............... 556/18 |
| 6,248,540 B1 | 6/2001 | Weinberg et al. ............ 435/7.1 |
| 6,260,407 B1 | 7/2001 | Petro et al. ................ 73/61.52 |
| 6,265,226 B1 | 7/2001 | Petro et al. ................ 436/180 |
| 6,265,601 B1 | 7/2001 | Guram et al. ............... 558/411 |
| 6,268,513 B1 | 7/2001 | Guram et al. ............... 549/200 |
| 6,294,388 B1 | 9/2001 | Petro ............................ 436/8 |
| 6,296,771 B1 | 10/2001 | Miroslav .................... 210/656 |
| 6,306,658 B1 | 10/2001 | Turner et al. ................. 436/37 |
| 6,315,923 B1 | 11/2001 | Devenney et al. ...... 252/314 R |
| 6,326,090 B1 | 12/2001 | Schultz et al. .............. 428/688 |
| 6,393,898 B1 * | 5/2002 | Hajduk et al. ............. 73/54.05 |
| 6,412,336 B2 * | 7/2002 | Shin et al. ................. 73/54.07 |
| 6,484,566 B1 * | 11/2002 | Shin et al. ................. 73/54.07 |

OTHER PUBLICATIONS

"Standard Test Method for Rubber Property–International Hardness," American Society for Testing and Materials.

Amitay–Sadovsky, Ella and H. Daniel Wagner, "Evaluation of Young's Modulus of Polymers from Knoop Microindentation Test" Polymer Communications, 1998, vol. 39, No. 11, pp. 2387–2390.

Calleja, F.J. Balta, "Microhardness Studies of Polymers and Their Transitions" TRIP, Dec. 1994, vol. 2, No. 12, pp. 419–425.

Bowlt, C., "A Simple Capillary Viscometer" Physics Education, Mar. 1975, vol. 10, No. 2, pp. 102–103.

Lacombe, Robert H. and Jeremy Greenblatt, "Mechanical Propoerties of Thin Polyimide Films" pp. 647–668.

Shinozaki, D.M. and Y. Lu, "Micro–Indentation Relaxation Measurements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl. Phys. Jun. 15, 1984, 55 (12).

European Search Report dated Dec. 10, 2001.

U.S. application Ser. No. 09/420,334 entitled "Graphic Design of Combinatorial Material Libraries" (Lacy, et al.) filed on Oct. 18, 1999.

U.S. patent application Ser. No. 09/305,830 titled "Synthesizing Combinatorial Libraries of Materials" (Rust, et al.) filed on May 5, 1999.

U.S. application Ser. No. 09/550,549 entitled "Automated Process Control And Data Management System And Methods" (Crevier, et al.) filed on Apr. 14, 2000.

U.S. application Ser. No. 09/755,623 entitled "Laboratory Database System and Methods For Combinatorial Materials Research" (Dorsett, Jr., et al.) filed on Jan. 5, 2001.

The family of applications for U.S. application Ser. No. 09/227,558 entitled, "Apparatus and Method of Research for Creating and Testing Novel Catalysts, Reactions and Polymers" (Turner et al.) filed Jan. 8, 1999.

U.S. application Ser. No. 09/235,368 entitled "Polymerization Method From the Combinatorial Synthesis and Analysis of Organometallic Compounds and Catalysts" (Weinberg et al.) filed on Jan. 21, 1999.

U.S. Provisional application Ser. No. 60/122,704 entitled "Controlled, Stable Free Radical Emulsion and Water-Based Polymerizations" (Klaerner et al.) filed on Mar. 9, 1999.

The family of applications for U.S. application Ser. No. 09/567,598 entitled "Polymer Libraries on a Substrate, Method for Forming Polymer Libraries on a Substrate and Characterization Methods with Same" (Boussie et al.) filed May 10, 2000.

The family of applications for U.S. patent application Ser. No. 09/174,856 titled "Graphic Design of Combinatorial Material Libraries" (Lacy, et al.) filed on Oct. 19, 1998.

Odian, Principles of Polymerization, 3rd Ed., John Wiley & Sons, Inc. (1991).

Timoshenko, S., Theory of Plates and Shells, McGraw-Hill, New York 1940.

U.S. patent application Ser. No. 09/939,404 entitled "High Throughput Mechanical Property and Bulge Testing of Material Libraries," (D. Hajduk et al.) filed on Aug. 24, 2001.

U.S. patent application Ser. No. 09/939,252 entitled "High Throughput Mechanical Rapid Serial Property Testing of Material Libraries," (P. Mansky) filed on Aug. 24, 2001.

U.S. patent application Ser. No. 09/939,139 entitled "High Throughput Fabric Handle Screening," (M. Kossuth et al.) filed Aug. 24, 2001.

U.S. patent application Ser. No. 09/939,263 entitled "High Throughput Mechanical Property Testing of Materials Libraries Using Capacitance," (D. Hajduk et al.) filed on Aug. 24, 2001.

U.S. patent application Ser. No. 09/938,994 entitled "High Throughput Mechanical Property Testing of Materials Libraries Using a Piezoelectric," (D. Hajduk) filed on Aug. 24, 2001.

The family of applications for U.S. patent application Ser. No. 09/580,024 entitled "Instrument for High Throughput Measurement of Material Physical Properties and Method of Using Same," (Carlson, et al.) filed on May 26, 2000.

The family of applications for U.S. patent application Ser. No. 09/174,856 titled "Graphic Design of Combinatorial Material Libraries" (Lacy, et al.) filed on Oct. 19, 1998.

U.S. application Serial No. 09/801,165 entitled "Method and Apparatus for Characterizing Materials By Using a Mechanical Resonator" filed Mar. 7, 2001.

U.S. application Ser. No. 09/578,997 entitled "High Throughput Viscometer and Method of Using Same" filed May 25, 2000.

PCT application No. PCT/US01/11417 entitled "Automated Process Control And Data Management System And Methods", filed Apr. 6, 2001.

Young, W.C., Roark's Formulas for Stress and Stain, 1989.

Osterberg, Peter M. and Stephen D. Senturia, "M–TEST: A Test Chip for MEMS Material Property Measurement Using Electrostatically Acutated Test Structures," Journal of Microelectromechanical Systmes, vol. 6, No. 2, Jun. 1997.

Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

Grover, G. et al., "A Screening Technique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Process for Handle Measurement," Textile Research Journal 62(5), pp. 279–290 (1992).

"Handle–O–Meter", Thwing–Albert Instrument Company, Philadelphia, PA.

Raeel, Mastura and Jiang Liu, "An Empirical Model for Fabric Hand" Textile Research Journal 62, 1, pp. 31–38 (1991).

Ali, S.I. and Shahida Begum, "Fabric Softeners and Softness Perception", Ergonomics, v.37, No. 5, pp. 801–806 (1994).

* cited by examiner

this part has been omitted for brevity,

HIGH THROUGHPUT RHEOLOGICAL TESTING OF MATERIALS

TECHNICAL FIELD

The present invention generally relates to the field of materials characterization. In particular, the invention relates to high throughput screens for evaluating the rheological properties of a material.

BACKGROUND OF THE INVENTION

Currently, there is substantial research activity directed toward the discovery and optimization of polymeric materials for a wide range of applications. Although the chemistry of many polymers and polymerization reactions has been extensively studied, it is, nonetheless, rarely possible to predict a priori the physical or chemical properties a particular polymeric material will possess or the precise composition and architecture that will result from any particular synthesis scheme. Thus, characterization techniques to determine such properties are an essential part of the discovery process.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

With the development of combinatorial techniques that allow for the parallel synthesis of arrays comprising a vast number of diverse industrially relevant materials, there is a need for methods and devices and systems to rapidly characterize the physical and mechanical properties of the samples that are synthesized, such as the viscosity or related rheological properties of a material. There is also a particular need to reduce time involved in analyzing samples when transfer of the sample between locations is necessary. It would be especially attractive to rapidly test a plurality of samples on a common substrate, without needing to remove the samples from the substrate.

The characterization of materials using combinatorial methods has only recently become known. Examples of such technology are disclosed, for example, in commonly owned U.S. Pat. Nos. 6,182,499 (McFarland et al); 6,175,409 B1 (Nielsen et al); 6,157,449 (Hajduk et al); 6,151,123 (Nielsen); 6,034,775 (McFarland et al); 5,959,297 (Weinberg et al), all of which are hereby expressly incorporated by reference herein.

A high throughput viscometer is taught in U.S. application Ser. No. 09/578,997, filed May 25, 2000 ("High Throughput Viscometer and Method of Using the Same") hereby expressly incorporated by reference herein.

SUMMARY OF THE INVENTION

In accordance with one preferred embodiment of the present invention, a library of materials is screened for rheological properties, such as viscosity. A force is applied to a library of materials while the materials reside within their respective regions of a common substrate. The relative flow resistance of the materials is measured in response to the force; and the materials in the library are analyzed and ranked based on the monitored flow resistance.

In another preferred embodiment, a plurality of liquid samples is screened for viscosity, where a library is provided having at least four different samples, and the viscosity of each of the samples is measured serially at a throughput rate no greater than about 10 minutes per sample.

In another preferred embodiment, a plurality of liquid samples is screened for viscosity, where a library is provided having at least four different samples, and the viscosity of at least two of the samples is measured simultaneously at a throughput rate no greater than about 10 minutes per library.

DETAILED DESCRIPTION OF THE PREFERRED EMBODIMENT

I. Glossary

The following terms are intended to have the following general meanings as they are used herein.

1. Substrate: A material or structure having a rigid or semi-rigid surface. In many embodiments, the substrate will have physically separate regions for different materials with, for example, dimples, wells, trenches, or the like. The regions will preferably be no greater than about 1 liter, and more preferably will be smaller than about 0.1 liter, more preferably smaller than about 0.01 liter and still more preferably smaller than about 0.001 liter. One preferred substrate useful in accordance with the present invention is a microtiter plate having a plurality of wells, and at least preferably 8×N wells, where N is an integer 1 or higher. Another preferred substrate useful in accordance with the present invention is a vial rack supporting a plurality of vials.

2. Viscosity: A measure of a resistance of a fluid to flow when subjected to a force, and preferably one for inducing a shear stress. Reference herein to viscosity is not intended to exclude the employment of viscosity measurements to the determination of other properties recognized as interdependent upon the measurement of viscosity, including but not density, temperature dependent properties of materials, pressure dependent properties of material, velocity/flowrate dependent properties of materials or the like.

These and other aspects of the invention are to be considered exemplary and non-limiting, and are discussed in greater detail below. The several aspects of the characterization methods and systems disclosed and claimed herein can be advantageously employed separately, or in combination to efficiently characterize a variety of materials, with particular emphasis on polymeric materials. In preferred embodiments, these features are employed in combination to form a materials characterization system that can operate as a high-throughput screen in a materials science research program directed to identifying, characterizing or optimizing new or existing materials. Certain characterizing information—particularly those obtainable from the present invention are broadly useful for characterizing polymers and polymerization reactions. As such, the particular materials and/or mechanisms disclosed herein should be considered exemplary of the invention and non-limiting as to the scope of the invention, which may be applicable in a variety of applications.

Combinatorial Approaches for Research

In a combinatorial approach for identifying or optimizing materials or preparation conditions, a large compositional space (e.g., with respect to polymers, of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing libraries and then rapidly screening such libraries. By way of illustration, polymer libraries can comprise, for example, polymerization product mixtures resulting from polymerization reactions that are varied with respect to such factors.

Combinatorial approaches for screening a library can include an initial, primary screening, in which product mixtures are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard material or preparation scheme. Because local performance maxima may exist in compositional spaces between those evaluated in the primary screening of the first libraries or alternatively, in process-condition spaces different from those considered in the first screening, it may be advantageous to screen more focused libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused libraries can continue as long as the high-throughput primary screen can meaningfully distinguish between neighboring library compositions or compounds.

Once one or more hits have been satisfactorily identified based on the primary screening, libraries focused around the primary-screen hits can be evaluated with a secondary screen—a screen designed to provide (and typically verified, based on known materials, to provide) chemical process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular compositions, reactants, additives, processing conditions or post-synthesis processing conditions having characteristics that surpass the predetermined metrics for the secondary screen may then be considered to be "leads." If desired, additional libraries focused about such lead materials can be screened with additional secondary screens or with tertiary screens. Identified lead compositions, reactants, additives, processing conditions or post-synthesis processing conditions may be subsequently developed for commercial applications through traditional bench-scale and/or pilot scale experiments.

While the concept of primary screens and secondary screens as outlined above provides a valuable combinatorial research model, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary, secondary or other screen, depending on the specific research program and goals thereof. See, generally, U.S. patent application Ser. No. 09/227,558 entitled "Apparatus and Method of Research for Creating and Testing Novel Catalysts, Reactions and Polymers", filed Jan. 8, 1999 by Turner et al., for further discussion of a combinatorial approach to polymer science research.

According to the present invention, methods, systems and devices are disclosed that improve the efficiency and/or effectiveness of the steps necessary to characterize mechanical or physical properties of samples or a plurality of samples (e.g., libraries of samples). In preferred embodiments, a property of a plurality of samples or of components thereof can be analyzed in a characterization system with an average sample-throughput sufficient for an effective combinatorial science research program.

In accordance with one preferred embodiment of the present invention, an array of materials is screened for viscosity. An array of materials is provided. The array is contacted with at least one capillary for permitting the materials to be drawn into the capillary. A first force is applied to the materials while present in the capillary. The relative flow resistance of the materials in the capillary is measured in response to the force; and the materials in the library of materials are ranked or otherwise compared with each other or another material based on the monitored flow resistance.

Various protocols may be employed involving some or all of the aforementioned steps. For example, a sample may be analyzed either with preparation or without preparation. Additionally it should be recognized that sequences other than the order of steps listed above are possible, and the above listing is not intended as limiting.

As a general approach for improving the sample throughput for a plurality of samples (e.g., polymer samples), each of the steps applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

The throughput of a plurality of samples through a single step in a characterization process is improved by optimizing the speed of that step, while maintaining—to the extent necessary—the information-quality aspects of that step. Although conventional research norms, developed in the context in which research was rate-limited primarily by the synthesis of samples, may find such an approach less than wholly satisfactory, the degree of rigor can be entirely satisfactory for a primary or a secondary screen of a combinatorial library of samples. For combinatorial research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, in a rapid-serial approach for characterizing a sample, sample delivery to a substrate for a second sample in a series can be effected before or while the first sample in the series is being screened. As another example, a screen of a second sample in a series can be initiated while the first sample in the series is being screened. These approaches, as well as others, are discussed in greater detail below.

A characterization protocol for a plurality of samples can involve a single-step process (e.g., direct measurement of a property of a sample or of a component thereof). In a rapid-serial screen approach for a single-step process, the plurality of samples and a single measuring instrument or other apparatus are serially positioned in relation to each other for serial analysis of the samples. In a parallel detection approach, two or more measuring instruments or other apparatus are employed to measure a property of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, the same property of another subset of four or more samples is screened in parallel. It will be recognized, of course, that plural measuring instruments can be employed simultaneous, or plural measuring instruments can be employed serially.

For characterization protocols involving more than one step, optimization approaches to effect high-throughput characterization can vary. As one example, a plurality of samples can be characterized with a single characterization system (I) in a rapid-serial approach in which each of the plurality of samples ($s_1, s_2, s_3 \ldots s_n$) are processed serially through the characterization system (I) with each of the steps effected in series on each of the of samples to produce a serial stream of corresponding characterizing property information ($p_1, p_2, p_3 \ldots p_n$). This approach benefits from minimal capital investment, and may provide sufficient throughput—particularly when the steps have been optimized with respect to speed and quality of information.

As another example, a plurality of samples can be characterized with two or more instruments in a pure parallel (or for larger libraries, serial-parallel) approach in which the plurality of samples ($s_1, s_2, s_3 \ldots s_n$) or a subset thereof are processed through the two or more measurement systems (I, II, III . . . N) in parallel, with each individual system effecting each step on one of the samples to produce the property information ($p_1, p_2, p_3 \ldots p_n$) in parallel. This approach is advantageous with respect to overall throughput, but may be constrained by the required capital investment.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified by parallel sample preparation of a plurality of samples ($s_1, s_2, s_3 \ldots s_n$), followed by measuring a property with a single apparatus to produce a serial stream of corresponding characterizing property information ($p_1, p_2, p_3 \ldots p_n$). In another exemplary parallel-series hybrid approach, a plurality of samples ($s_1, s_2, s_3 \ldots s_n$) are prepared, measured and correlated in a slightly offset (staggered) parallel manner to produce the characterizing property information ($p_1, p_2, p_3 \ldots p_n$) in the same staggered-parallel manner.

Optimization of individual characterization steps with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel characterization protocols.

Material Samples

The materials screened in the present invention include polymeric materials, organic materials, amorphous materials, crystalline materials, macromolecular materials, small-molecule materials, inorganic materials, pure materials, mixtures of materials or the like.

The present invention may be used to screen or test most any flowable material that may be a commercial product itself or may be an ingredient or portion within a commercial product. Exemplary commercial products, which may be tested or may include ingredients that may be tested according to the present invention include pharmaceuticals, coatings, cosmetics, adhesives, inks, foods, crop agents, detergents, protective agents, lubricants and the like. Polyelectrolytes or polyampholytes may also be screened.

In a particularly preferred embodiment, the present invention is employed for screening flowable samples. The invention thus has particular utility in connection with the screening of a number of different material forms including, for example, gels, oils, solvents, greases, creams, ointments, pastes, powders, films, particles, bulk materials, dispersions, suspensions, emulsions or the like. The invention can be used to analyze the resulting properties of a particular flowable sample material or the relative or comparative effects that an additive or environmental condition has upon a particular flowable sample material (e.g., the effect of a detergent, a flow modifier, or the like).

In another particularly preferred embodiment, the present invention is employed for screening polymer samples, or plastic samples including polymers. Accordingly, unless otherwise stated, reference to screening of polymers or other processing of polymers includes plastics incorporating such polymers. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest. Blends of polymers may also be analyzed in accordance with the present invention.

In one embodiment, the polymer molecule of the polymer component is preferably a non-biological polymer, though biological polymers may also be screened in accordance with the present invention. A non-biological polymer is, for purposes herein, a polymer other than an amino-acid polymer (e.g., protein) or a nucleic acid polymer (e.g., deoxyribonucleic acid (DNA)). Though the employment of the present invention for screening of materials for use as biological implants is contemplated. The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule.

The particular composition of the polymer molecule is not critical, the material may be thermoplastic, thermoset or a mixture thereof. It may be a polycondensate, polyadduct, a modified natural polymer, or otherwise. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or and an additional phase which may be a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of affects of variations of additives upon the characteristics of the material. The various components of the heterogeneous polymer sample can be uniformly or nonuniformly dispersed in the continuous fluid phase.

In one embodiment, useful in connection with the screening of polymers, at a point prior to, during, or after depositing the sample onto the substrate, the sample is preferably treated to form a flowable sample, such as a polymer solution, a polymer emulsion, a polymer dispersion or a polymer that is liquid in the pure state (i.e., a neat polymer), or a melt. A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being an emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 um to about 1000 um, more typically from about 0.4 um to about 500 um, and even more typically from about 0.5 um to about 200 um. Exemplary polymers that can be in the form of neat polymer samples include dendrimers, and siloxane, among others. The liquid polymer sample can also be employed in the form of a slurry, a latex, a microgel a physical gel, or in any other form sufficient for creating an array for screening analysis as described and claimed herein.

In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semicrystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g. temperature moisture, radiation, chemicals, etc.), aged, or the like.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 1000 micrograms, even more typically from about 5 micrograms to about 100 micrograms, and still more typically from about 20 micrograms to about 50 micrograms.

When placed on a substrate for forming an array, as discussed herein with regard to sampling, the samples may be dispensed with any suitable dispensing apparatus (e.g. an automated micropipette or capillary dispenser, preferably with a heated tip). Each sample of the array is dispensed to an individually addressable region on the substrate. Preferably each sample occupies no more than about 1000 mm$^2$, more preferably no more than about 100, more preferably no more than about 20 mm$^2$ of planar area on a substrate surface, more preferably no more than about 5 mm$^2$, and shall more preferably no more than about 0.5 mm$^2$. In applications where the sample is disposed in a well, preferably the sample size does not exceed about 20 milligrams.

Accordingly, for some applications, the individual samples are each typically no greater than about 20 ml, more preferably no greater than about 5 ml and still more preferably no greater than about 0.5 ml.

Libraries of Samples

A plurality of samples comprises 2 or more samples that are physically or temporally separated from each other—for example, by residing in different regions of a substrate, in different sample containers, by having a membrane or other partitioning material positioned between samples, or otherwise. The plurality of samples preferably comprises 4 or more samples and more preferably 8 or more samples. Four samples can be employed, for example, in connection with experiments having one control sample and three samples varying (e.g., with respect to composition or process conditions as discussed above) to be representative of a high, a medium and a low-value of the varied factor—and thereby, to provide some indication as to trends. Four samples are also a minimum number of samples to effect a serial-parallel characterization approach, as described above (e.g., with two detectors operating in parallel). Eight samples can provide for additional variations in the explored factor space. Moreover, eight samples corresponds to the number of parallel polymerization reactors in the PPR-8™, being selectively offered as one of the Discovery ToolS™ of Symyx Technologies, Inc. (Santa Clara, Calif.), which can be used to prepare polymers for screening in accordance with the present invention. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of other parallel reactor configurations for synthesizing polymers for screening herein (e.g., the PPR-48™, Symyx Technologies, Inc.) and/or of standard sample containers (e.g., 96-well microtiter plate-type formats). Moreover, even larger numbers of samples can be characterized according to the methods of the present invention for larger scale research endeavors. Hence, the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples, and preferably from about 8 samples to about 10,000 samples. In many applications, however, the number of samples can range from about 80 samples to about 1500 samples. In some cases, in which processing of samples using typical 96-well microtiter-plate formatting is convenient or otherwise desirable, the number of polymer samples can be 96*N, where N is an integer ranging from about 1 to about 100. For many applications, N can suitably range from 1 to about 20, and in some cases, from 1 to about 5.

The plurality of samples can be a library of samples. A library of samples comprises an array of two or more different samples spatially separated—preferably on a common substrate, or temporally separated. Candidate samples (i.e., members) within a library may differ in a definable and typically predefined way, including with regard to chemical structure, processing (e.g., synthesis) history, mixtures of interacting components, post-synthesis treatment, purity, etc. The samples are spatially separated, preferably at an exposed surface of the substrate, such that the array of samples are separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial chemistry research applications, at least two or more, preferably at least four or more, even more preferably eight or more and, in many cases most, and allowably each of the plurality of samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of the samples included in the library are different from each other. Still more preferably, the library includes at least 48 samples and at least 90% of the samples included in the library are different from each other.

The substrate can be a structure having a rigid or semi-rigid surface on which or into which the array of samples can be formed or deposited. The substrate can be of any suitable material, and preferably includes materials that are inert with respect to the polymer samples of interest, or otherwise will not materially affect the mechanical or physical characteristics of one sample in an array relative to another. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. Stainless steel or another metal, or ceramics such as silicon including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In preferred embodiments, the substrate is designed such that the individually addressable regions of the substrate can act as polymerization or other suitable reaction vessels for preparing a product mixture, as well as sample containers for the in-situ analysis of two or more different samples during subsequent characterization thereof. Glass-lined, 96-well, 384-well and 1536-well microtiter-type plates, fabricated from stainless steel and/or aluminum, are preferred substrates for a library of liquid or polymer samples. The choice of an appropriate specific substrate material and/or form for certain applications will be apparent to those of skill in the art in view of the guidance provided herein.

The library of materials can be a combinatorial library of product mixtures. Libraries can comprise, for example, product mixtures resulting from reactions that are varied with respect to, for example, reactant materials (e.g., monomers, comonomers), catalysts, catalyst precursors, initiators, additives, the relative amounts of such components, reaction conditions (e.g., temperature, pressure, reaction time), post-synthesis treatment, or any other factor affecting polymerization or material properties. Design variables for polymerization reactions are well known in the art. See generally, Odian, Principles of Polymerization, 3rd Ed., John Wiley& Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227, 558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT Pat. Application WO 96/11878.

The libraries can be advantageously characterized directly, without being isolated, from the reaction vessel in which the sample was prepared or synthesized.

While such methods are preferred for a combinatorial approach to research, they are to be considered exemplary and non-limiting. As noted above, the particular samples characterized according to the methods and with the apparatus disclosed herein can be from any source, including, but not limited to polymerization product mixtures or other liquids, including those resulting from combinatorial synthesis approaches.

Analytical Instrument

The protocols for characterizing one or more samples preferably further comprise determining a property of interest from the detected property based upon the resulting viscosity measurements. The physically-detected properties, can be correlated to properties of interest. Such properties of interest include, without limitation, rheological properties such as viscosity, viscoelasticity (e.g., shear dependent viscoelasticity), shear thinning, shear thickening, yield, stress and the like. Other properties of interest may include, without limitation, melt index, thermal degradation, aging characteristics, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius, radius of gyration, chemical composition, amounts of residual monomer, presence and amounts of other low-molecular weight impurities in samples, particle or molecular size, intrinsic viscosity, molecular shape, molecular conformation, and/or agglomeration or assemblage of molecules. The correlation between a measured viscosity and a determined property of interest can be based on mathematical models and/or empirical calibrations. Such correlation methods are generally known in the art.

The aforementioned characterizing properties of interest can, once determined, be mathematically combined in various combinations to provide figures of merit for various properties or attributes of interest. Other combinations of the fundamental characterization properties of interest will be apparent to those of skill in the art.

Figure 1:
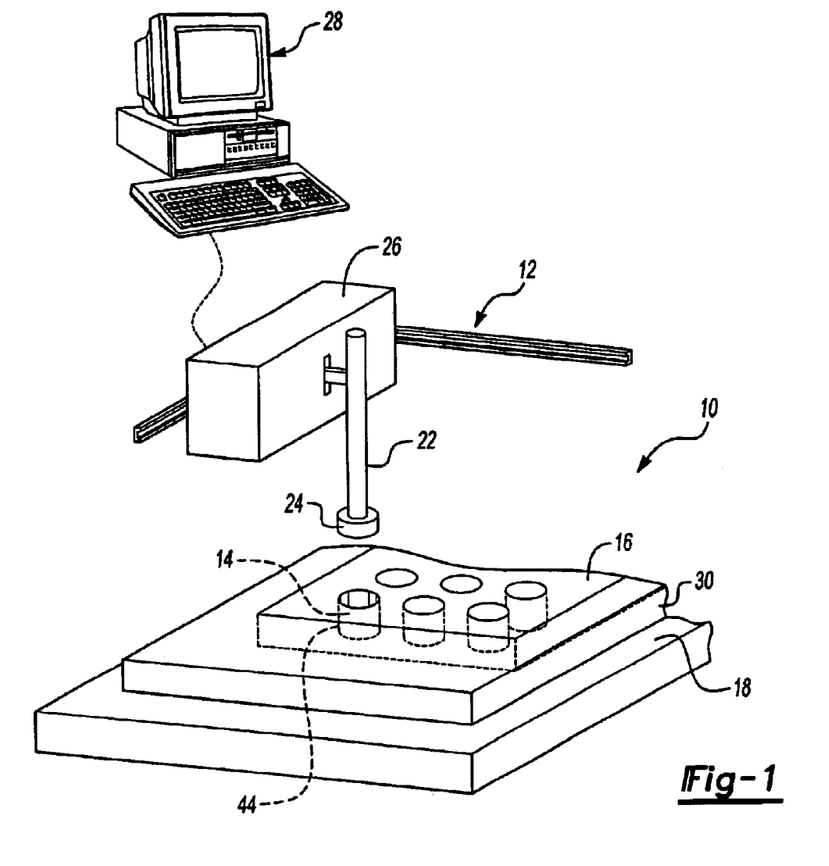
FIG. 1 is a schematic of an analytical system in accordance with the present invention.

Referring to FIG. 1, the system 10 of the present invention includes a force applicator 12 for applying a force to a sample 14 in an array of samples on a substrate 16, and a device 18 for measuring the response of the sample to the force. More specifically, and with reference to FIG. 2, a preferred instrument 20 of the present invention includes a translatable plunger 22 with a tip portion 24 for applying a pressure upon a sample. It will be appreciated that samples are provided to the substrate in any suitable manner, such as by a robot or an otherwise automated fluid dispenser.

Figure 2:
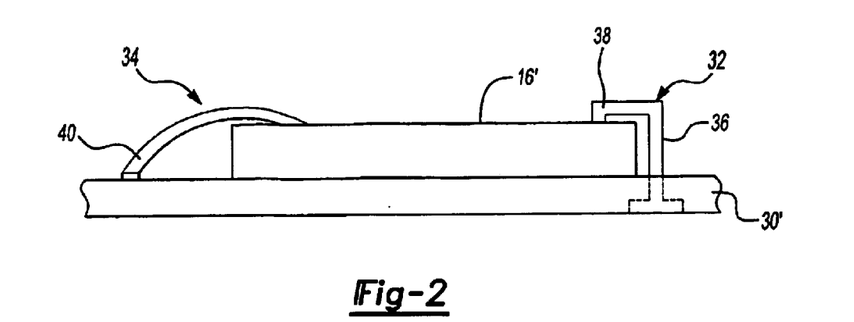
FIG. 2 is a schematic of one preferred measuring instrument used in the present invention.

In one preferred embodiment, the translatable plunger is drivingly connected to a suitable motor for driving the plunger 22 serially into the samples. The motor may be directly connected to the plunger or it may be connected to intermediate linkage in direct driving engagement with the plunger. By way of example, a suitable robotic system is employed, such as an XYZ robot arm available commercially from suppliers such Cavro Scientific Instruments, Inc. (Sunnyvale, Calif.). Such device has multiple axis range of motion, and more preferably at least motion in the orthogonal x, y, z coordinate axes system. One or more suitable stepper motors or servo motors may be employed in addition to or alternative to the CAVRO robotic system. A microprocessor or other like computer is programmed for directing the robot relative to the respective locations of members of an array. Alternatively an automatic auto-sampler instrument may be suitably adapted for use such as auto-samplers commercially available from Agilent Technologies. Optionally, the same or a different robot may be employed for transferring samples to the substrate and thereafter analyzing them.

By way of example, in a particularly preferred embodiment, a robot 28 is programmably employed (e.g., using one or more types of software, such as IMPRESSIONIST™, or EPOCH™, available from Symyx Technoloies, Inc.) for rapid serial testing of a plurality of samples in an array. For instance, the robot 28 directs the plunger 22 to a first sample. The plunger 22 is passed through the first sample and then removed. The plunger optionally is then washed or flushed to remove residue from a previous sample or the plunger is optionally replaced if disposable plungers are used. The process is repeated for a second sample and consecutively thereafter with the remaining samples to be tested.

It will be appreciated that the robot may itself include a motor for driving the plunger. Alternatively, the robot may be employed for two axis translation of the plunger with one or more additional motors or other suitable actuators for directly driving the plunger in the third of the orthogonal axes. A motor may also be employed as desired for suitable rotational translation.

Figure 3:
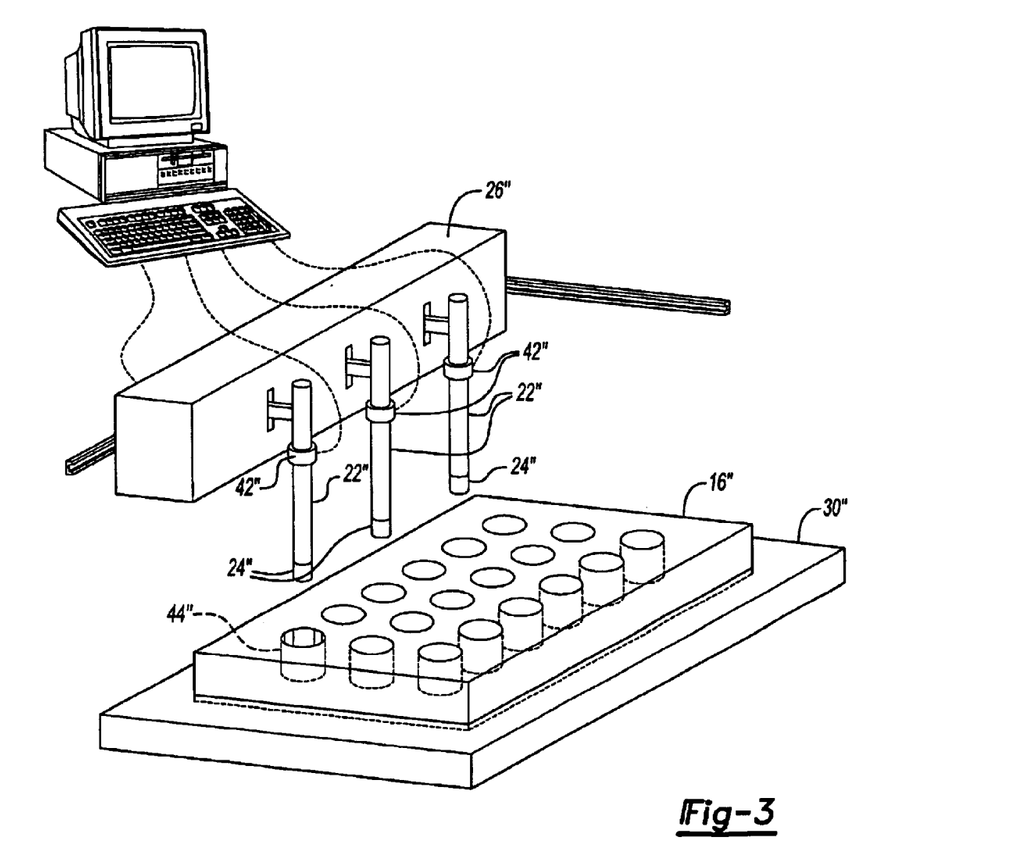
FIG. 3 is a schematic of another alternative analytical system in accordance with the present invention.

In yet another embodiment it is possible to rest a substrate of specimens upon a mounting stage (or load cell) that is translatable relative to a fixed capillary or plunger. It is also possible to employ a translatable mounting stage or load cell and a capillary or plunger in combination. In this regard, and with further reference to FIG. 2, a suitable substrate holder 30 is employed for positioning the samples held by the substrate 16 relative to the plunger 22. For instance, a substrate such as a microtiter plate might nestingly reside in the holder 30, which may itself be associated with a load cell. Alternatively, as illustrated in FIG. 3 (without limitation upon the embodiment in which it might be employed) a stage 32 might be employed for receiving a substrate. The stage 32 preferably includes a suitable structure 34 for securing the substrate in place during sampling, such as a clamp, a mechanical fastener arrangement or the like.

Regardless of the drive system employed, it should be sufficient to induce a testing force of about 0.001 KN to about 100 KN and more preferably at least about 0.1 KN to about 20 KN. It shall be understood, however that a variety of testing forces may be induced depending upon the drive system or other factors. Further, preferably the plunger speed ranges from about 0.001 to about 1500 mm/min and more preferably about 0.01 to about 1000 mm/min, and still more preferably about 1 to about 100. The drive system is capable of operating at temperatures to at least about 400° C.

The force measurement device may include one or more suitable measuring devices including conventional load cells, pressure transducers, sensors, detectors or the like. A single measuring device may be employed to measure the relative displacement of a sample in response to the force induced by the plunger.

Referring to FIG. 1, for rapid serial testing a highly preferred system employs one or more load cells 30 upon which a substrate 16 is placed. A single plunger 22 is employed, with the robot consecutively relocating the plunger 22 and samples in the array relative to each other. The load cell may be a single load cell common to each sample or well. The load cell may be a single load cell with individually addressable regions corresponding to each sample or well. Each sample may be assigned its own load cell or a plurality of load cells may be used wherein each is assigned to a plurality of samples.

Alternatively or in addition to the other measuring devices, the plunger itself may include a suitable measuring device. The plunger or plungers may be fitted with a load cell, pressure transducer or any other suitable measuring device.

While the present invention lends itself especially well to rapid serial testing, parallel testing (i.e., testing of two or more samples simultaneously) may be employed alternatively or in combination with rapid serial testing. Of course, suitable modifications will be appropriate. For instance, a plurality of plungers can be employed for simultaneous positioning relative to the array of samples. Preferably, a suitable pressure transducer or other sensor or detector is employed for measuring resistance to flow in a sample of an individual plunger in view of a known applied force. In this manner, multiple samples can be tested at once.

Any suitable art disclosed measuring device may be employed. Typically, measuring devices such as load cells, pressure transducers and the like can be chosen from many commercially available devices depending on where it is desirable to mount or place the devices.

The measurement device preferably is equipped to output a signal or readout correlating with a measurement. The output might be visually readable from the device itself (e.g., an integrated LED, LCD or like display). It might be outputted as an electrical signal that is converted to a voltage for driving a control unit, microprocessor or the like, or otherwise communicates with a computer into which the measuring device output is entered for sorting, storing, comparing, analyzing or the like. Such computer may be separate from or integrated with any control or computer used for driving the plunger, or for delivering samples to a substrate.

Figure 1A:
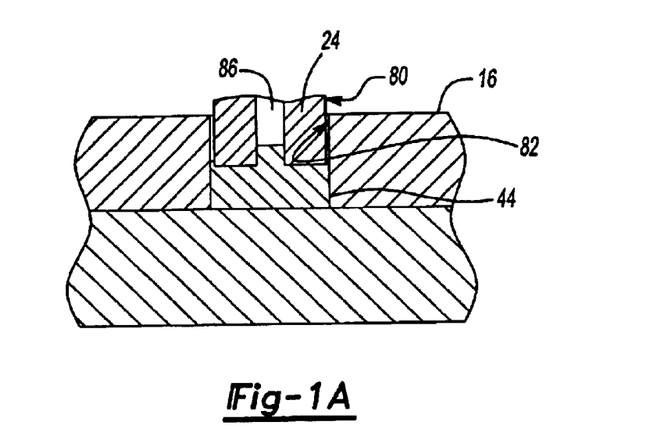
FIG. 1(a) is a magnified sectional view of a well of the system of FIG. 1 having a probe located within the well.
Figure 4A:
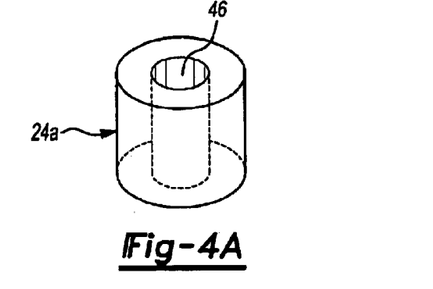
FIGS. 4(a)–4(h) illustrate perspective views of several alternative tip portions for a plunger.

The plungers of the present invention are specifically adapted for use with fluids in individual members of sample libraries on a substrate. As discussed, one highly preferred embodiment employs a microtiter plate or a suitable receptacle or vial supporting rack as the substrate. Accordingly, a preferred plunger for the application is configured for applying force to a fluid (e.g., liquid) in the respective wells of the microtiter plate or wells of the receptacles (e.g., vials). More particularly, referring to FIGS. 1(a) and 4(a), the preferred plunger is configured at a tip portion 24 to substantially matingly fit within a well 44 of the microtiter plate 16. Close tolerances are desired between the outer wall 80 of the plunger tip portion 24 and an inner wall 82 of a well 44. Preferably, the tolerances are such that any parasitic conductance of fluid in gaps between the plunger outer wall and well inner wall (or elsewhere in the plunger) is statistically negligible relative to the primary fluid conductance observed.

The plunger employed in the present invention thus may employ any of a number of suitable tip portion configurations that permit fluid passage into and through at least a portion of it. By way of example, referring again to FIGS. 1(a) and 4(a), one tip portion 24 might be constructed to permit passage of fluid through a central axial bore 86. The tip portion thus has an outer diameter that approximates the diameter of each well of a microtiter plate. Accordingly, the wall defining the microtiter plate well serves as a guide surface for the tip portion. In this example the tip portion preferably is a sufficiently rigid structure to reduce the potential for incidental deflection of the tip portion upon force application, which might affect the integrity of the measurement. However, it is possible that the tip portion may be made in whole or in part of a more flexible material, so that sealing may be accomplished between the plunger and the wall of a well, thereby directing the fluid through the central bore 86.

Figure 4B:
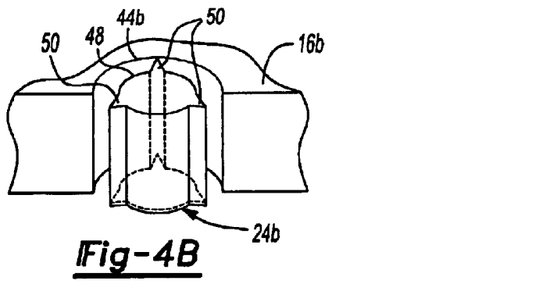

In another embodiment, shown in FIG. 4(b), the tip portion is configured to have an outer wall 48 that is spaced from the inner wall 44(b) of a well over some or all of its outer periphery. The spacing is maintained through the use of a suitable positioning device for keeping the tip portion centered in the well. More preferably, a spacer structure is employed, such as a plurality of radial spacing projections (e.g., fins) 50. Referring to the example of FIGS. 4(b) and 4(d), though configurations with one or two radial spacing projections are possible, more preferably, three or more radial projections are employed to help provide axial stability.

Figure 4C:
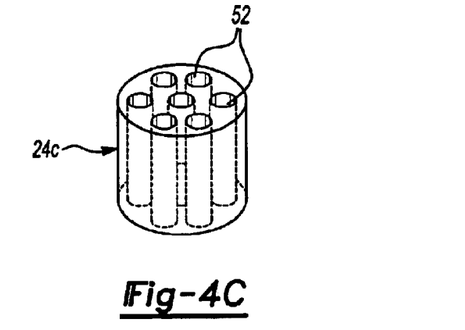
Figure 4D:
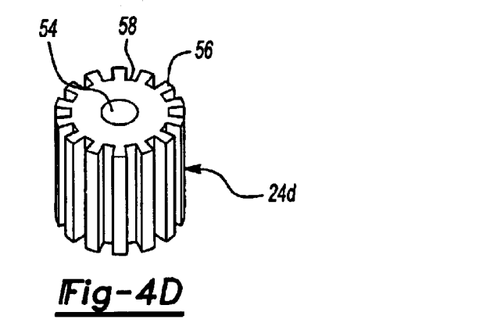
Figure 4E:
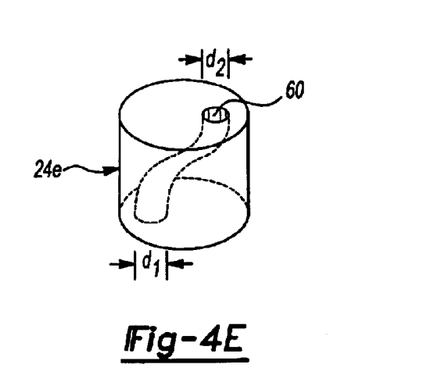
Figure 4F:
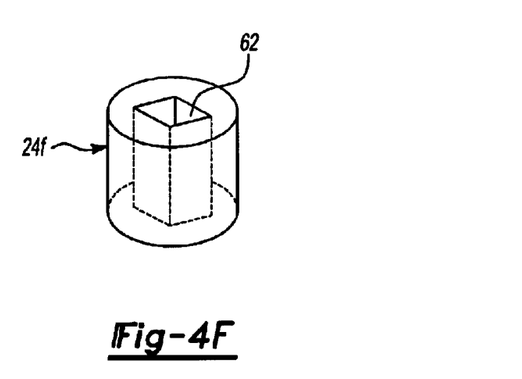

Any of a number of other configurations may be employed including a plurality of axial bores as shown in FIG. 4(c), elongated slot shaped passageways as shown in FIG. 4(f), passageways that vary in size or configuration along the axis of the plunger as shown in FIG. 4(e), composites of the examples of FIGS. 4(a)–4(f) or other configurations. The plunger preferably is made of a suitable metal, plastic or ceramic material, and may be coated or uncoated over some or all of its surface that is to contact the test fluid. Preferably it is made of an epoxy or epoxy based material. It may be coated or uncoated, smooth or roughened or otherwise treated for modifying its surface characteristics over some or all of its inner or outer surfaces. The dimensions of the overall plunger are not critical. However, in one preferred embodiment, for use in screening samples directly in a microtiter plate, the ratio of length to diameter ranges from about 5:1 to about 100:1. It may be desirable in some instances to control the ratio of the relative amount of surface area as between a lead face of a tip portion and the area of the walls defining the axial passageway. For example, such ratio might range from about greater than 20:1, and more preferably about 50:1.

It may be preferable for the tips to include vertical walls on its outer periphery or on its inner periphery defining one or more bores. It may also be preferable for the bores to of the tips to be the same size in circumstances where more than one tip is used or where a tip includes multiple bores.

Figure 4G:
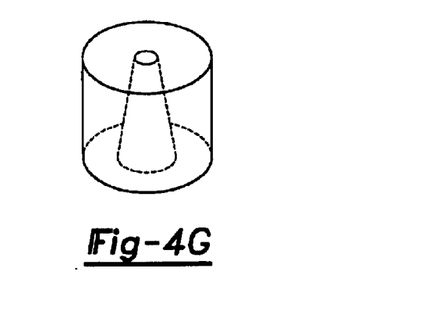
Figure 4H:
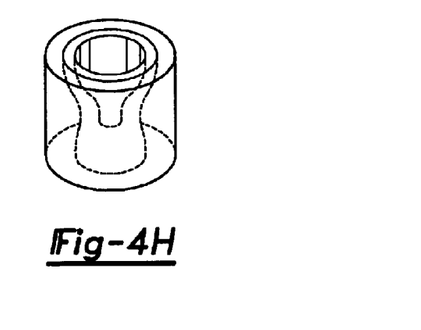

In still other alternatives shown in FIGS. 4(g)–4(h), bores may be tapered to have progressively smaller cross-sectional areas further up the tip.

As can be appreciated from the above, in operation, the rheological or viscosity properties of a fluid, and preferably an array of fluid samples can be measured while the samples are physically located on a substrate. For instance, in a preferred embodiment, samples are synthesized in an array of wells and then tested in the same array of wells Alternatively, the samples may be prepared elsewhere and then transferred to the array of wells, such as by manually or using an automated sampler as described herein. According to either of these embodiments one or more automatic systems (e.g., robots) may be used for preparation of samples, testing of samples or both.

While the sample is in the well, and without the need to withdraw it from the well, the plunger is moved up or down in the fluid at a known velocity, which may be variable, but is preferably constant. The plunger tip portion is configured so that as it moves through the fluid, the fluid on the leading side (i.e., the side that is forward relative to the plunger movement direction), is forced to flow through the passageways defined in or about the plunger. The fluid thus flows from the leading side to the trailing side of the plunger as the plunger is advanced, all the while remaining resident within the well of the substrate. Preferably, the flow of the fluid continues until a dynamic equilibrium is reached between the pressure in the plunger and the pressure outside the plunger.

The pressure required to create the flow is produced by the downward force of plunger. In turn, the response of the fluid is measured by the load cell or a suitable sensor located in sensing relationship beneath the substrate, directly or indirectly on the plunger, or both. From the measurements alone, it is possible to obtain comparative data as between samples of an array. Such data may be compiled and samples grouped by or otherwise ranked in order of their relative performance. Taking into account known information such as the plunger velocity, geometry of container, sample size, channel size and the like, quantitative rheological properties can also be determined or calculated.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample, though slower throughput is within the present invention. As used in connection herewith, the term "average sample throughput" refers to the sample-number normalized total (cumulative) period of time required to detect a property of two or more polymer samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample, still more preferably not more than about 2 minutes per sample and even still more preferably about 15 to 30 seconds per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled sample library synthesis rates. It is generally desirable that combinatorial screening systems, such as the characterization protocols disclosed herein, operate with roughly the same sample throughput as combinatorial synthesis protocols—to prevent a backlog of uncharacterized product samples. Hence, to illustrate, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of samples at such throughputs can offer sufficiently rigorous quality of data, to be useful for scientifically meaningful exploration of the materials, compositions, formulations, compounds and/or reaction conditions.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently screen a sample or component thereof having a particularly desired property (e.g., such as weight-average molecular weight). In short, the search can be accelerated for the particular property of research interest.

In other embodiments viscosity is measured at an average sample-throughput of not more than 60 minutes per library, more preferably not more than 10 minutes per library, and still more preferably not more than 2 minutes per library. Even more preferred, the viscosity is measured at an average sample-throughput of not more than 60 seconds per library, more preferably not more than 30 seconds per library, and still more preferably not more than 10 seconds per library.

Calibration Methods and Standards

As desired the systems and methods of the present invention may optionally employ a calibration procedure. By way of example, a calibration standard is provided having a number of subcomponents that differ with respect to viscosity. Such subcomponents are typically referred to as "known standards" or, simply, "standards" that are well characterized with respect to the calibrating property of interest. They are analyzed by the viscosity measuring apparatus of the present invention and the apparatus is adjusted as desired.

Other Screens

The present invention may be employed by itself or in combination with one or more other screening protocols (e.g., using the same instrument with an interchangeable test fixture, or a different instrument) for the analysis of polymers, liquids or their consitituents. Without limitation, examples of such screening techniques include those addressed or identified in commonly-owned U.S. Pat. Nos. 6,182,499 (McFarland et al); 6,175,409 B1 (Nielsen et al); 6,157,449 (Hajduk et al); 6,151,123 (Nielsen); 6,034,775 (McFarland et al); 5,959,297 (Weinberg et al), 5,776,359 (Schultz et al.), all of which are hereby expressly incorporated by reference herein.

It should be understood that the invention is not limited to the exact embodiment or construction which has been illustrated and described but that various changes may be made without departing from the spirit and the scope of the invention.

What is claimed is:

1. A method of screening a library of materials for viscosity, the method comprising:

providing a library of materials in a plurality of wells defined on a common substrate;

contacting members of said library with at least one capillary for permitting said materials to be passed through a tip portion of said capillary;

applying a first force to said materials;

monitoring the relative flow resistance of said materials in response to said force, while said materials remain on said substrate and without the need to remove said materials from said substrate applying a second force to said library of materials during monitoring; and ranking members of said library based on the monitored flow resistances.

2. A method for measuring the viscosity of a plurality of liquid samples, said method comprising the steps of:

providing a library comprising at least four different liquid samples;

contacting said liquid samples with at least one capillary for permitting said liquid samples to be passed through a tip portion of said capillary;

applying a first force to said liquid samples; and serially measuring the viscosity of each of said samples at a throughput rate no greater than about 10 minutes per sample, while said materials remain on said substrate and without the need to remove said materials from said substrate.

3. The method of claim 2 wherein said liquid samples are selected from the group consisting of polymer solutions, polymer emulsions and polymer dispersions.

4. The method of claim 2 wherein said liquid samples are members of a combinatorial library of polymerization product mixtures.

5. The method of claim 2 wherein said liquid samples include at least 8 different samples.

6. The method of claim 2 wherein said liquid samples include at least 16 different liquid samples.

7. The method of claim 2 said polymer samples include at least 96 different liquid samples.

8. The method of claim 2 wherein said viscosity is measured at an average sample-throughput of not more then about 8 minutes per sample.

9. The method of claim 2 wherein said viscosity is measured at an average sample-throughput of not more than about 5 minutes per sample.

10. The method of claim 2 wherein said viscosity is measured at an average sample-throughput of not more than about 2 minutes per sample.

11. The method of claim 2 wherein said viscosity is measured at an average sample-throughput of not more than about 50 seconds per sample.

12. The method of claim 2 wherein said viscosity is measured at an average sample-throughput of not more than about 30 seconds per sample.

13. A method for measuring the viscosity of a plurality of liquid samples, said method comprising the steps of:

providing a library comprising at least four different liquid samples, contacting said liquid samples with at least one capillary for permitting said liquid samples to be passed through a tip portion of said capillary; and serially measuring the viscosity of each of said samples at en average sample-throughput of not more then about 10 seconds per sample.

14. The method of claim 2 wherein said liquid sample comprises a solid component having a particle diameter ranging from about 1 nm to about 500 nm.

15. A method for measuring the viscosity of a plurality of liquid samples, said method comprising the steps of:

providing a library comprising at least four different liquid samples, contacting said liquid samples with at least on capillary for permitting said liquid samples to be passed through a tip portion of said capillary; and serially measuring the viscosity of each or said samples at a throughput rate no greater than about 10 minutes per sample, wherein said liquid sample comprises a solid component having a particle size ranging from about 5 nm to about 300 nm in diameter.

16. The method of claim 2 wherein each said sample is no greater than a out 10 ml.

17. The method of claim 2 wherein each said sample is no greater than about 2 ml.

18. A method of screening a library of materials for viscosity, the method comprising:

providing a library of at least 16 materials in a plurality of wells defined on a common substrate wherein at least one or more wails define a perimeter of the plurality of wells and wherein each of said plurality of wells has a diameter no larger than about 10 mm;

contacting the at least 18 materials of said library with at least one capillary in a rapid serial manner for permitting said at least 18 materials to be passed through a substantially cylindrical opening extending through one or more tip portions of the at last one capillary wherein the one or more tip portions are contacted with the at least 16 materials by positioning the one or more tip portions within the plurality or wells such that an outer wail of the one or more tip portions is in substantially mating relationship with the at least one or more wails that define the perimeter of the plurality of wells;

applying a first force to the at least 16 materials that causes the at least 18 materials to flow through the one or more tip portions of the, at least one capillary tube;

measuring the relative flow resistances of the at least 16 materials in response to the force, while the at least 16 materials remain on the substrate and without the need to remove the at least 16 materials from the substrate wherein the relative flow resistances are measured at a throughput rate of no greater than 4 minutes per sample; and ranking each of the at least 16 materials relative to each other based on the measured flow resistance.

* * * * *

UNITED STATES PATENT AND TRADEMARK OFFICE
CERTIFICATE OF CORRECTION

PATENT NO. : 6,769,292 B2
DATED : August 3, 2004
INVENTOR(S) : Paul Mansky and Damian Hajduk

It is certified that error appears in the above-identified patent and that said Letters Patent is hereby corrected as shown below:

Column 19,
Line 47, "50" should be -- 60 --

Column 20,
Line 12, "on" should be -- one --
Lines 15 and 39, "or" should be -- of --
Line 22, "a out" should be -- about --
Lines 29 and 42, "wails" should be -- walls --
Lines 32, 34 and 46, "18" should be -- 16 --
Line 36, "last" should be -- least --
Line 40, "wail" should be -- wall --

Signed and Sealed this

First Day of February, 2005

JON W. DUDAS
*Director of the United States Patent and Trademark Office*